Feb. 12, 1974 J. S. SWEET Plant Pat. 3,480
POINSETTIA PLANT
Filed Oct. 16, 1972
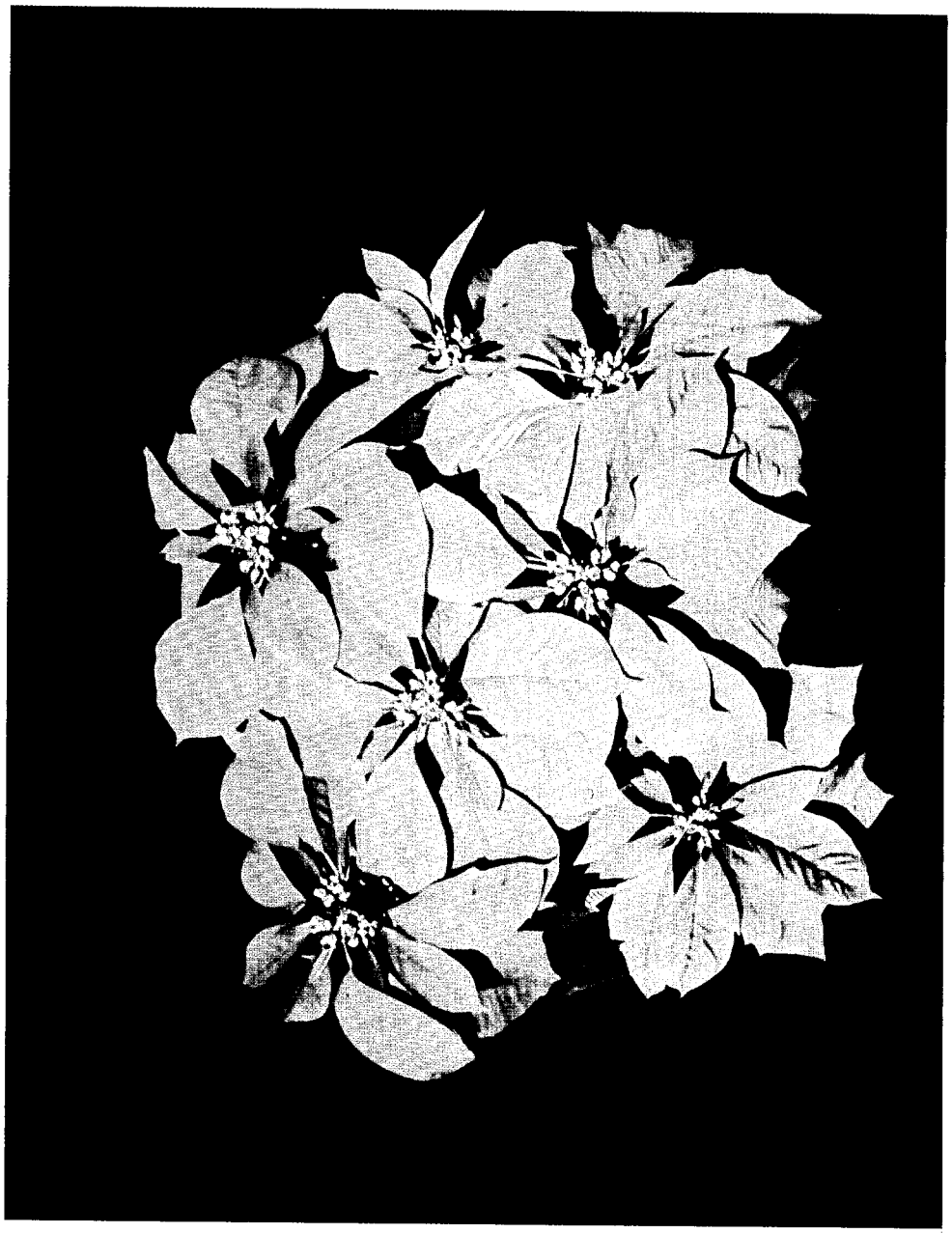
INVENTOR
Jack S. Sweet
by: Myron P. Laughlin.
Attorney United States Patent Office Plant Pat. 3,480
Patented Feb. 12, 1974

3,480
POINSETTIA PLANT

Jack S. Sweet, St. Petersburg, Fla., assignor to Earl J. Small Growers, Inc., Pinellas Park, Fla.

Filed Oct. 16, 1972, Ser. No. 298,436
Int. Cl. A01h 5/00
U.S. Cl. Plt.—86 1 Claim This invention relates to marketable poinsettia plants of the species *Euphorbia pulcherrima.*

The present invention is for a new and distinct variety of poinsettia plant of the species *Euphorbia pulcherrima,* produced and originated by cross-breeding two different red seedlings with the definite goal of creating a new strong-growing and free-branching poinsettia plant variety.

In selecting poinsettia plants for breeding, it was primarily objective that the final result give horticulture a new poinsettia plant suitable for pot growth production that would branch freely, have very compact growth habit, that would not require chemical height control, that would have strong branches that would not break off, and would retain such inherent qualities in both bracts and foliage. All of these objects were achieved in this new poinsettia seedling, a distinct new variety that distinguishes itself from both its parents, while retaining important characteristics of each:

I have now produced and disclose herein a new, compact plant with close-set, shortened internodes and strong stiff upright stem characteristics;

A new plant that has shown an extraordinary ability for close branching that freely produces 6 to 8 stems from a single pinched plant;

This novel new plant supplies many wide bracts which form an influorescence on each branch, and present a beautiful massed effect of multiple blooms arising from a single plant;

This novel mass plant produces long-lasting effect of both bracts and foliage, producing a long period benefit to the general public in home decoration for months after normal maturity, even though subjected to accidental violence;

This novel new plant propagates and roots freely from vegetative cuttings retaining all its valued new characteristics through succeeding asexual reproduction;

This new plant is capable of accurate timing so that it blooms readily in early December to take full advantage of the prime poinsettia demand season and sets its bud easily, even under abnormally high or low greenhouse temperatures that tend to delay the flowering of other known poinsettia varieties;

The herein disclosed new plant has a strong root system capable of withstanding excessive watering, and extensive shipping fatigue while still presenting a more vigorous and long lasting product for the benefit of the general public in decoration, a product whose decorative values will not be quickly deteriorated by the minimal care given in the average household.

The accompanying photograph shows a typical specimen of my new variety with the colors being reproduced as closely as available photographic methods can define, with developed multiple bract formations produced from a single branched plant, pinched only one time in mid September and flowered in early December. The colors in this photograph and appended descriptive matter are coded from the Nickerson Color Fan (Munsell Color Co.), except where common dictionary significance will be obvious.

The description and photographs are taken from specimens asexually reproduced under my direction through natural growth in greenhouses at Pinellas Park in Florida, U.S.A.

Parentage: Seedling

*Seed parent.*—A seedling designated in my records as #310 (a descendant of a commercial variety known as "C–1"—Plant Pat. No. 2,923).

*Pollen parent.*—A selected red seedling of unknown parentage.

Growth habit: Upright growth with extremely close internodes to give a shortened height characteristic suitable for pot culture without the need for chemical growth regulators. A distinctive growth characteristic of this plant is its ability to make 6 to 8 perfect branches from a single small pinched plant, all very stiff and erect in habit while requiring no staking or artificial support.

Root foundation: This new poinsettia has a vigorous root system capable of withstanding more abuse than existing varities, particularly as regards excessive watering without losing firm root support.

Bloom season: The first week in December appears to be the natural blooming time for this new poinsettia, thus giving maximum beauty to the public for the entire Christmas season.

Foliage: The leaves are alternate, closely set on short internodes with somewhat shortened and stiff petioles. Typical leaves vary from lanceolate-ovate to oak leaf in shape. The apices are sharply acuminate as are the teeth on the outer end of major lateral veins. The leaf color on mature leaves is ("dark yellowish green" #2.5 G–4/6) on the upper side and ("strong yellowish green" #2.5 G–5/9) on the underside.

Inflorescence: The bract involucre is very brilliant red ("strong red" #5–4/12) on the upper side and ("strong red" #2.5–5/12) on the lower side. The bracts are very broadly ovate ending in acuminate apices and are held out stiffly horizontal for long periods without drooping, even after bracts continue to age. They also hold their color exceedingly well during several months in a typical home.

Flowers: The cyathia are borne compactly in the center of the bracts and do not tend to spread apart with age of the inflorescence. The individual flowers are approximately one-quarter inch in size and are ("vivid greenish yellow" #7.5 Y–8/12). The nectar cups are ("vivid yellow" #5Y–8/12), while the stamens are ("dark red" #5R–3/7). The pollen color is ("vivid yellow" #5Y–8/12).

SUMMARY

This new variety also has a unique ability to produce a multiple larger mass potted plant through the use of several plants per pot whereby it performs as a "single stem" variety of multiple quality with very stiff stems and many leaves on closely set internodes. Thus this new plant has the ability to produce a pinched plant that will be naturally short without chemical shorteners, that will branch with 6 to 8 breaks from a single pinch and maintain its stiffness right to the customer's home. The individual branched stems are much stronger than other "free branching" varieties and do not readily break off in transit.

I claim:

1. A new and distinct variety of poinsettia plant substantially as illustrated and described, produced by selective cross breeding for a compact plant with short internodes, a strong, stiff stem structure that branches freely from a single pinch to produce a compact multiple inflorescence with a massive display of bracts.

No references cited.

ROBERT E. BAGWILL, Primary Examiner